US007556933B2

(12) United States Patent
Cairns et al.

(10) Patent No.: US 7,556,933 B2
(45) Date of Patent: Jul. 7, 2009

(54) REAGENT SYSTEM AND PROCESS FOR ADENOSINE TRIPHOSPHATE MONITORING

(75) Inventors: James C Cairns, Toronto (CA); Phillip J Whalen, Lower Kingsclear (CA); Patrick A Whalen, Fredericton (CA)

(73) Assignee: Luminultra Technologies Ltd., New Brunswick (CA)

( * ) Notice: Subject to any disclaimer, the term of this patent is extended or adjusted under 35 U.S.C. 154(b) by 216 days.

(21) Appl. No.: 10/957,276

(22) Filed: Oct. 1, 2004

(65) Prior Publication Data

US 2006/0073537 A1  Apr. 6, 2006

(51) Int. Cl.
C12Q 1/66 (2006.01)
C12M 1/34 (2006.01)
C12M 3/00 (2006.01)
(52) U.S. Cl. .................... 435/8; 435/287.1; 435/810
(58) Field of Classification Search ............... 435/8
See application file for complete search history.

(56) References Cited

U.S. PATENT DOCUMENTS

| 4,014,745 | A | * | 3/1977 | Fletcher et al. ............... 435/8 |
| 5,258,285 | A | * | 11/1993 | Aegidius ............... 435/8 |
| 5,558,986 | A | | 9/1996 | Lundin |
| 6,004,767 | A | | 12/1999 | Crouch et al. |
| 6,780,418 | B1 | * | 8/2004 | Fahey et al. ............... 424/248.1 |
| 6,812,012 | B1 | * | 11/2004 | Hattori et al. ............... 435/189 |
| 6,924,300 | B2 | * | 8/2005 | Momose et al. ............ 514/365 |
| 2001/0046687 | A1 | * | 11/2001 | DiCesare ............... 435/8 |
| 2002/0165186 | A1 | * | 11/2002 | Hauber et al. ............... 514/44 |
| 2004/0224377 | A1 | * | 11/2004 | Hawkins et al. ............... 435/8 |

FOREIGN PATENT DOCUMENTS

WO  WO 94/11528  5/1994

OTHER PUBLICATIONS

Lundin, A., "Optimised Assay of Firefly Luciferase With Stable Light Emission in Bioluminescence and Chemiluminescence Status Report," A.A. Szaly, L.J. Kricka, and P. Stanley ed., Wiley, pp. 291-295 (1993).

Wang C.Y. and Andrade, J.D., "Purification and Preservation of Firefly Luciferase," A. Campbell, et al., eds., Bioluminescence and Chemiluminescence, Wiley, Abstract only (1994).
Patterson, James W.; Brezonik, Patrick L.; and Putnam, Hugh D., "Measurement and Significance of Adenosine Triphosphate in Activated Sludge," Environmental Science & Technology, vol. 4, No. 7, pp. 569-575, dated Jul. 1970.
Roe, Jr., Patrick C.; and Bhagat, Surinder K., "Adenosine triphophate as a control parameter for activated sludge processes," Journal WPCF, vol. 54, No. 3, pp. 244-254, dated Mar. 1982.
Tobin, R. S.; Ryan, J. F.; and Afghan, B. K., "An Improved Method For The Determination Of Adenosinetriphosphate In Environmental Samples," Water Research, vol. 12, pp. 783-792, dated 1978.
Archibald, F., Methot, M., Young, F. and Paice, M.G., "A Simple System To Rapidly Monitor Activated Sludge Health And Performance," Wat. Res. 35 (10), pp. 2543-2553 (2001).
"Standard Test Method For Adenosine Triphosphate (ATP) Content of Microorganism in Water," Annual Book of ASTM Standards, vol. 11.02 Water (II), pp. 455-458 (1989).
"Adenosine 5'-Triphosphate (ATP) Bioluminescent Assay Kit", Sigma Chemicals, Technical Bulletin # BAAB-1 (1988).
rLuciferase/Luciferin Reagent Bioluminescence Detection Reagent for ATP Measurement, Promega Corporation Technical Bulletin #268 (2001).
Tobin, R.S., Ryan, J.F. and Afghan, B.K., "An Improved Method For Quantitative Measurement of ATP and Its Application to Measure Microbial Activity in Natural Waters, Activated Sludges, and Sediments," G. Borun (ed.) Second Bi-Annual ATP Methodology Symposium, SAI Technology Co., San Diego, California, Pub Date 1977.
Deluca, M., ATP Methodology Seminar, SAI Technology Co., San Diego (1975).

* cited by examiner

Primary Examiner—Herbert J. Lilling
(74) Attorney, Agent, or Firm—Sandra P. Thompson; Buchalter Nemer (57) ABSTRACT

A reagent system comprises a first reagent which includes a high pH phosphate buffer, and a second reagent which includes luciferase, luciferin, a magnesium salt and an enzyme stabilizer. The second reagent has a low pH and a buffer with a pK which is near the optimum pH for activity of luciferase. The reagent system may be used in a process for measuring total adenosine triphosphate (ATP) and/or dissolved extracellular ATP, in a fluid containing microorganisms. The reagent system may also be used in a microbiological remediation or production process.

31 Claims, 8 Drawing Sheets

Fig. 1 Dissolved ATP in a Sewage Treatment Plant Reactor

Fig. 2 Alkaline pH Stress

Fig 3: Effect a 7-day addition of glucose and nutrient feed on Biomass Stress Index

Fig.4 DO deprivation stress:
Biomass Stress Index

Fig.5 DARR activity reduces dATP

Fig. 6 planktonic ATP test

Fig. 8 Stability of Luciferase Reagent Formulations

REAGENT SYSTEM AND PROCESS FOR ADENOSINE TRIPHOSPHATE MONITORING

FIELD OF THE INVENTION

The invention relates to reagent systems and processes for adenosine triphosphate (ATP) monitoring.

BACKGROUND OF THE INVENTION

Microorganisms have been harnessed for a variety of beneficial processes such as the production of foods, beverages and pharmaceuticals, and the remediation of air, soil and water.

The factors that influence these processes may include the presence and quality of food and nutrients, the presence and quantity of toxic chemicals, the degree of aeration, pH, and temperature. These factors may interact in an additive, synergistic, or antagonistic manner. In bioremediation processes, the situation is further complicated because the medium to be treated is often highly complex and variable.

Effective monitoring technologies are an important component of a successful biological process. They form the tools to build a stable and efficient biological process. Most powerful is a technology that provides information of the effects of operating environment on the microorganisms. Statistical process analyses on the data generated from such a technology can be used to solve problems and enable continual process improvement.

ATP is the keystone of metabolic activity. Most of the energy for microbial processes microorganisms is stored and transmitted via ATP. ATP is produced as microbial food is consumed and is utilized for cell maintenance and the synthesis of new cells and biochemicals.

ATP is most easily measured by the firefly luciferase assay. The reaction is as follows:

in which,

ATP=Adenosine triphosphate

AMP=Adenosine monophosphate

PPi=pyrophosphate

The chemical energy produced from the breakdown of ATP is converted into light energy. Each molecule of ATP consumed in the reaction produces one photon of light. This light output can be quantified in a luminometer.

ATP measurement has been proposed as a tool to assist in the process control of biological waste treatment systems for over 3 decades (1-3). Generally, the concept has been to substitute ATP as a more accurate estimate of the amount of viable biomass in the reactor of a biological wastewater treatment facility. This has been commonly estimated by measuring the volatile suspended solids (VSS).

However, the concepts in these references have never included measurements of dissolved ATP (d-ATP) or extracellular ATP. All analyses have been performed measuring total ATP (t-ATP), which is the combination of intracellular ATP plus extracellular ATP. Dissolved ATP analyses have been used in sanitation monitoring, but only as a measure of non-microbial ATP from food sources. Similarly, in microbial growth control, dissolved ATP has been monitored, but only in the presence of conditions that are highly lethal to microorganisms.

In addition, reagents for simple but accurate measurement of dissolved and total ATP have not been optimized for biological process monitoring. Biological remediation and production processes differ from the mainstream applications of ATP analyses—sanitation monitoring and microbial growth control—in that samples contain up to 1000 times higher levels of biomass or greater. Furthermore, biological wastewater samples contain many substances that interfere with the firefly luciferase assay for measuring ATP.

Reagent formulations containing luciferase and luciferin for assaying ATP in a sample are known in the art. For example, U.S. Pat. No. 6,004,767 of Crouch et al. discloses a bioluminescent reagent as a freeze dried powder, to be reconstituted prior to use. U.S. Pat. No. 5,558,986 of Lundin discloses such reagent formulation for use in combination with a cyclodextrin. US patent application No. 2001/0046687 of DiCesare also discloses the use of such formulation, wherein trehalose is used to enhance the emission of light intensity. Published international patent application, WO 94/11528 of Foote and Grant discloses an aqueous composition including polyols for use in a bioluminescent assay by adding a strong buffer to give a pH which is close to the optimum pH for the luciferase reaction.

SUMMARY OF THE INVENTION

The inventors have now discovered a reagent system for the measurement of total and dissolved ATP from samples containing microorganisms. The reagent system comprises a luciferase formulation and a buffer formulation. The buffer formulation is used to prepare stable ATP solutions from the samples, and is later mixed with the luciferase formulation to provide an efficient and reliable quantification of sample ATP concentration.

Total and dissolved ATP analyses then provide the basis for the control of biological remediation and production processes. The reagent can also be used in kits.

Accordingly, the invention provides in one aspect, a reagent system comprising: a first reagent which includes a high pH phosphate buffer; and a second reagent which includes luciferase, luciferin, a magnesium salt and an enzyme stabilizer. The second reagent has a low pH and a buffer with a pK which is near the optimum pH for activity of luciferase. Preferably, the high pH phosphate buffer may comprise a tribasic monovalent phosphate salt. This salt can be selected from the group consisting of trisodium phosphate, tripotassium phosphate, trilithium phosphate and combinations thereof. Other suitable salts may also be used.

In further embodiments of the reagent system according to the invention, the first reagent may further comprise a surfactant and/or a base. The surfactant can be a cationic surfactant or a non-ionic surfactant. A preferred cationic surfactant may be a quaternary ammonium salt such as benzalkonium chloride. Other suitable quaternary ammonium salts can also be used. A preferred non-ionic surfactant can be an octylphenol. The base may be a monovalent base selected from the group consisting of sodium hydroxide, potassium hydroxide, lithium hydroxide and combinations thereof.

In other embodiments of the reagent system according to the invention, the second reagent may further comprise a chelating agent. The enzyme stabilizer can be selected from the group consisting of an enzyme hydrogen-bond stabilizer, a protein enzyme stabilizer, a reducing agent and combinations thereof. A preferred hydrogen-bond stabilizer can be a polyol. The polyol can be selected from the group consisting of trehalose, glycerol, glycol and combinations thereof. Other suitable polyols may also be used. A preferred protein enzyme stabilizer can be selected from the group consisting of bovine serum albumin, casein and combinations thereof. A preferred chelating agent can be ethylenediamine tetra acetic acid (EDTA). The reducing agent can be selected from the group consisting of dithiothreitol, mercaptoethanol and combinations thereof.

In yet other embodiments of the reagent system according to the invention, the first reagent may have a pH which is greater than about 9.9. More particularly, the first reagent may have a pH of about 11.1 to 11.7. The pH of the second reagent may be adjusted to about pH 6 to 8.5, and its pK can be about 7.5 to 8.5. More particularly, the pH of the second reagent can be adjusted to about pH 7.0, and its pK can be 7.5 to 7.75.

In yet other embodiments of the reagent system according to the invention, luciferase can be a native luciferase or a recombinant luciferase. Optionally, the native luciferase can be obtained directly from fireflies. Luciferase can also be immobilized on a support substrate which can be a transparent material or a translucent material. These materials may be glass or silica. When luciferase is immobilized on a support substrate, it can be re-usable. The buffer of the second reagent can be selected from the group consisting of N-[2-hydroxyethyl]piperazine-N'-[2-ethanesulfonic acid] (HEPES), N-[tris(hydroxymethyl)methyl]glycine (TRICINE), N-[2-hydroxy-1,1-bis(hydroxymethyl)ethyl]glycine and combinations thereof. Other suitable buffers can also be used. Optionally, the second reagent can be reconstituted from a freeze-dried formulation.

In other embodiments of the reagent system according to the invention, the tribasic monovalent phosphate salt can be at a concentration of about 0.5 to 500 mM. More preferably, the monovalent phosphate salt can be at a concentration of about 5 mM. The chelating agent may be in an amount of about 0.03 to 1.3% by weight of the second reagent. The surfactant may be at a concentration of about 100 to 10,000 mg/L. More preferably, the surfactant can be at a concentration of about 1,000 to 4,000 mg/L. The base can be at a concentration of about 100 to 10,000 mg/L. More preferably the base can at a concentration of about 600 mg/L.

The invention provides, in a second aspect, a kit comprising: a first container having a first reagent which includes a high pH phosphate buffer; and a second container having a second reagent which includes luciferase, luciferin, a magnesium salt and an enzyme stabilizer. The second reagent has a low pH and a buffer with a pK which is near the optimum pH for activity of luciferase. In embodiments of the kit according to the invention, the first and second containers may have a low gas permeability. The reagents in the first and second containers may be in a single dose and ready for use.

Further, the first and second reagents in the kit of the invention may have the characteristics outlined above in relation to the first aspect of the invention.

According to a third aspect, the invention provides a process for measuring at least one of total ATP and dissolved extracellular ATP, in a fluid containing microorganisms, the process comprising the steps of: (a) obtaining a sample of the fluid; (b) mixing the sample with a first reagent that includes a high pH phosphate buffer to obtain a first mixture; (c) mixing the first mixture with a second reagent to obtain a second mixture, the second reagent including luciferase, luciferin, a magnesium salt and an enzyme stabilizer, and having a low pH and a buffer with a pK which is near the optimum pH for activity of luciferase; and (d) measuring the light produced in the second mixture using a luminometer.

In embodiments of the process according to the invention, a sub-sample of the first mixture may be obtained prior to step (c). More particularly, the sub-sample can be diluted prior to step (c). The fluid can be agitated, and/or the microorganisms from the fluid separated prior to step (a). Optionally, the separation step may further comprise a step selected from the group consisting of settling, filtration, flocculation, centrifugation and combinations thereof. Other suitable separation techniques may also be used.

The first and second reagents of the process of the invention may have the characteristics outlined above in relation to the first aspect of the invention.

According to a fourth aspect, the invention provides a method of controlling a microbiological remediation or production process, the method comprising the steps of: (a) obtaining a sample from a location in the process where it is desired to monitor microbiological characteristics; (b) analyzing the sample to obtain dissolved extracellular ATP concentration and total ATP concentration; (c) comparing the concentrations obtained in step (b) with at least one of the operational variables and outputs of the process; and (d) adjusting at least one process operational variable responsive to the result of step (c).

In embodiments of the method according to the invention, the location may be selected from the group consisting of process influent, anaerobic reactor, aerobic reactor, anaerobic reactor effluent, aerobic reactor effluent, anaerobic return, aerobic return, waste streams, clarifier effluent, settling basin and plant effluent. The operational variables may be selected from the group consisting of biodegradable substrate concentration, biological oxygen demand (BOD), chemical oxygen demand (COD), pH, acidity, alkalinity, temperature, conductivity, nutrients, chemical additions, dissolved oxygen concentration (DO), pressure, food to microorganism ratio, flow rate, toxic substance concentration and combinations thereof. The outputs may be selected from the group consisting of BOD removal, COD removal, nutrient consumption, heat, biomass yield, and concentration or production rate of carbon dioxide, methane, hydrogen, hydrogen sulfide, volatile fatty acids, organic acids, alcohols, suspended solids and volatile suspended solids.

The step of analyzing the sample to obtain dissolved and extracellular ATP concentration and total ATP concentration (step (b)) in the method of the invention, may further comprise the steps of: (i) measuring the dissolved extracellular ATP concentration; (ii) measuring the total ATP concentration; and (iii) subtracting the dissolved extracellular ATP concentration from the total ATP concentration to obtain the cellular ATP concentration. Optionally, the analyzing step may comprise the steps of: (i) measuring the dissolved extracellular ATP concentration; (ii) measuring the total ATP concentration; and (iii) calculating a ratio of dissolved extracellular ATP concentration to total ATP concentration to obtain a first stress index. The analyzing step may also comprise the steps of: (i) measuring the dissolved extracellular ATP concentration; (ii) measuring the total ATP concentration; (iii) subtracting the dissolved extracellular ATP concentration from the total ATP concentration to obtain the cellular ATP concentration; and (iv) calculating a ratio of dissolved extracellular ATP concentration to cellular ATP concentration to obtain a second stress index. Further, the analyzing step may comprise the step of pre-treating the sample prior to step (b) by: (i) adding a spike of dissolved ATP to the sample to obtain a mixture; and (ii) incubating the mixture.

In other embodiments of the method according to the invention, the mixture may be incubated for about 5 to 120 minutes, at a temperature which is within about 20° C. of the temperature range of the process environment from which the sample is obtained. The mixture can be incubated for about 10 minutes, at a temperature of about 20 to 30° C.

In the method of the invention, when the sample is pre-treated prior to the analyzing step, by adding a spike of dissolved ATP to the sample, the spike can be about 1 to 100 times higher than the total ATP concentration. More preferably, the dissolved ATP spike can be about 10 times higher than the total ATP concentration. The dissolved ATP spike can also be about 1 to 100 times higher than the cellular ATP concentration. More particularly the dissolved ATP spike can be about 10 times higher than the cellular ATP concentration.

In yet other embodiments of the method according to the invention, the pre-treatment step may comprise allowing the sample to settle by gravity, or subjecting the sample to centrifugation. More preferably, a flocculating agent can be added to the sample prior to settling. The flocculating agent can be selected from the group consisting of an aluminum salt, a ferric salt, a ferrous salt, an organic polymer and mixtures thereof. Other suitable flocculating agents may also be used. The organic polymer used as flocculating agent can be a high molecular weight cationic polymer selected from the group consisting of polyacrylamides, polydiallyldimethylammonium chlorides, polyethylenimines, polyamines and mixtures thereof. Other suitable high molecular organic polymers may also be used. The settling period may range from about 1 to 120 minutes. More particularly, the settling period can be about 10 minutes.

The pre-treatment step of the method according to the invention may comprise the step of pre-treating the sample prior to step (b) by passing the sample through at least one sieve to produce a filtrate, the sieve having a mesh with openings of about 2 to 1,000 microns. The sieve may have a mesh with openings of about 500 to 1,000 microns. Optionally, the sieve may have a mesh with openings of about 300 to 500 microns. The openings of the mesh can be about 20 to 80 microns or about 2 to 5 microns.

In other embodiments of the method according to the invention, the pre-treatment step may comprise: (i) sieving or treating the sample to obtain a floc containing excessive quantities of bulking filamentous bacteria; and (ii) re-suspending the floc in a liquid medium. Optionally, step (i) can be performed using a sieve which has a mesh with openings of about 300 to 600 microns. The liquid medium may include an influent water or culture medium that supports the growth or maintenance of filamentous bacteria.

In yet other embodiments of the method according to the invention, the sample may be obtained from a biological process reactor and the method may further comprise the step of pre-treating the sample prior to step (b) by: (i) diluting the sample in a process influent or effluent water to obtain a dilute sample; and (ii) incubating the dilute sample for at least one time interval period. The dilution range of the sample may be about 1 to 50%. The time interval period may range between about 10 minutes to 30 days. More particularly, the time interval period may range between about 10 minutes to 8 hours. The time interval period may also range between about 1 day to 30 days. The process influent or effluent water may be diluted with water prior to adding to the sample. Optionally, additional biodegradable matter and nutrients may be added to the process influent or effluent water prior to adding to the sample.

In yet other embodiments of the method according to the invention, the pre-treatment step may comprise: (i) adding a suspension of planktonic or free-floating bacteria to the sample to obtain a mixture; and (ii) incubating the mixture for at least 30 minutes. The incubation may be performed for about 5 to 120 minutes, at a temperature which may be within about 20° C. of the temperature range of the process environment from which the sample is obtained. More particularly, the mixture may be incubated for about 30 minutes to 3 days, and the temperature may be about 20 to 30° C.

Optionally, the above comparison step of the method according to the invention (step (c)) and/or the adjustment step (step (d)) may be accomplished through human interface or computer logic.

In other embodiments of the method according to the invention, the step of analyzing the sample to obtain dissolved extracellular ATP concentration and total ATP concentration may comprise the steps of: (i) mixing the sample with a first reagent that includes a high pH phosphate buffer to obtain a first mixture; (ii) mixing the first mixture with a second reagent to obtain a second mixture, the second reagent including luciferase, luciferin, a magnesium salt and an enzyme stabilizer, and having a low pH and a pK which is near the optimum pH for activity of luciferase; and (iii) measuring the light produced in the second mixture using a luminometer.

More particularly, the first and second reagents of the method of the invention may have the characteristics outlined above in relation to the first aspect of the invention.

The term "about" as used herein expresses a variation of which a person skilled in the art would know that the benefit of the invention will still be enabled.

BRIEF DESCRIPTION OF THE FIGURES

These and other advantages of the invention will become apparent upon reading the following detailed description and upon referring to the drawings in which.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE INVENTION

It has long been assumed that dissolved ATP would not be present under environmental conditions where life is supported. A publication by Holm-Hansen and Booth (4) is frequently cited by authors that make this assumption. However, because the samples in this publication were filtered prior to ATP analysis, much of the dissolved ATP would not have been measured.

In addition, other researchers have anticipated that dissolved ATP introduced into the reactor of a biological wastewater system would be rapidly degraded, and therefore have assumed that the dissolved ATP content of a reactor sample would be undetectable except under conditions that would kill the majority of microbial population.

Figure 1:
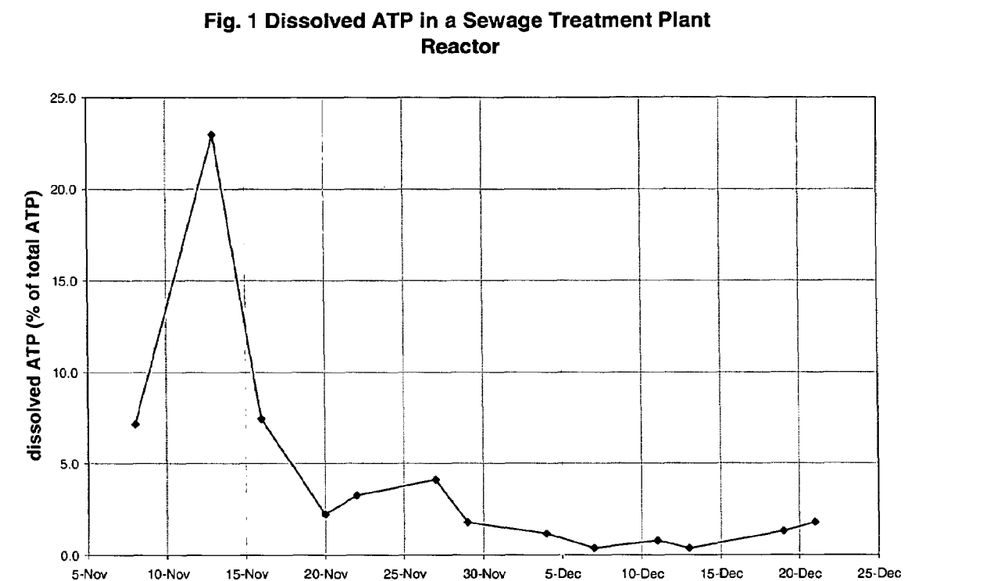
FIG. 1 illustrates the change over time of the amount of dissolved ATP in mixed liquor suspended solids samples from a sewage treatment plant reactor.

However, our experience has determined that this assumption is not correct, especially in biological wastewater treatment systems. FIG. 1 is a graph that shows the relative amount of dissolved ATP in mixed liquor suspended solids (MLSS) samples analyzed from the main reactor of an operating municipal sewage treatment system over a period of approximately two months. Dissolved ATP was measured by settling the biosolids, then measuring the ATP in the supernatant. Total ATP was measured by suspending the biosolids, adding an ATP releasing agent to the suspension, then measuring the ATP in the resulting solution. The details for the methods used to measure ATP are described later in this description.

It can be seen from FIG. 1 that during the first week of this test period, the dissolved ATP was greater than 20% of the total ATP. The dissolved ATP reached a minimum of 0.4% of the total ATP several weeks later, but was always at a measurable concentration.

We have discovered that measuring dissolved ATP in addition to total ATP not only provides a more accurate estimate of the viable biomass (because cellular ATP actually consists of total ATP minus dissolved ATP), but also can be applied in a variety of new ways to provide an indication of biomass health and settling properties.

For example, a pH that is too acidic or too alkaline is detrimental to a biological process. The laboratory experiment described below as Example 1 demonstrates how the stress of an adverse pH can be detected by monitoring the dissolved ATP together with total ATP.

EXAMPLE 1

The pH of the reactor MLSS sample was adjusted to near neutral, then dissolved ATP and total ATP were measured. Next, the sample pH was raised to pH 8.0 and the ATP tests were conducted again. This procedure was repeated several times, raising the pH by increments of approximately 0.5 units each time. During the entire experimental period, the sample was aerated to ensure an adequate supply of oxygen.

Figure 2:
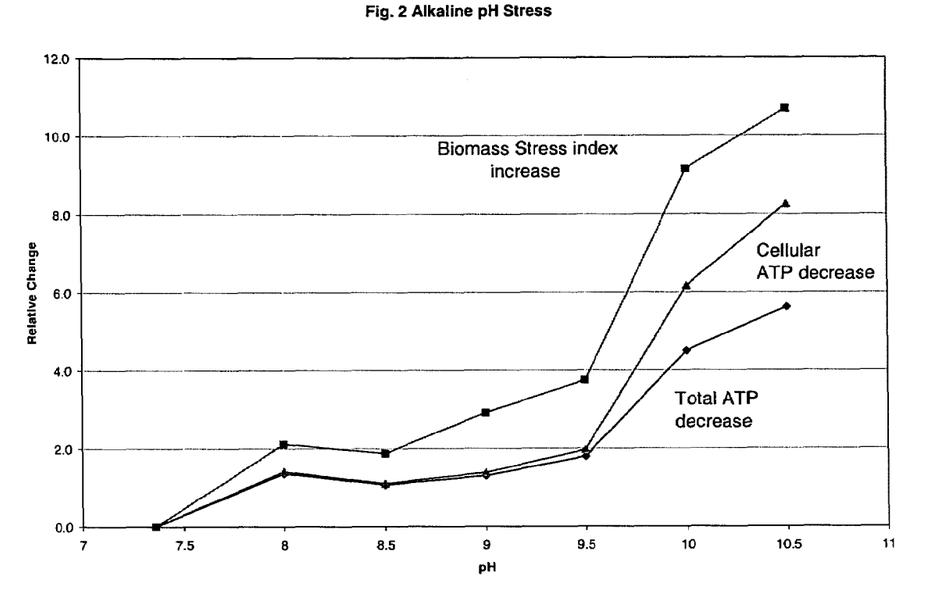
FIG. 2 illustrates the change in ATP parameters relative to the pH.

FIG. 2 shows the changes in three ATP parameters (total ATP, cellular ATP, and biomass stress index) relative to their values at the beginning of the experiment. The biomass stress index is the dissolved ATP calculated as a percentage of the total ATP.

For example, by the time the sample had been adjusted to pH 10.0, the total ATP of the sample had decreased by a factor 4.5, while the cellular ATP (total ATP minus dissolved ATP) had decreased by a factor of 6.2, and the biomass stress index increased by a factor of 9.0. The use of dissolved ATP to calculate cellular ATP as done in applications for microbial growth control is not as valuable for detecting stress to microbial population as the index developed here. For example, as indicated above, the change in biomass stress index is more dynamic than cellular ATP. In addition, even minor changes from the more favorable neutral pH could be rapidly detected by using the biomass stress index, whereas there was no difference in using the cellular ATP measurement until the pH exceeded pH 9.5, a condition known to be lethal to many microorganisms.

While it is important to detect environments that are adverse or hostile to microbial growth, detection of favorable environments is equally important in process optimization.

An experiment described below as Example 2 demonstrates the importance of monitoring total ATP together with dissolved ATP for this purpose.

EXAMPLE 2

Two bench-scale reactors were filled with samples that had recently been obtained from the reactor of a municipal sewage plant. The reactors were maintained at ambient temperature, continuously aerated, and the pH was adjusted daily to pH 7.0-7.1. One of the reactors was fed daily with 2,000 mg/L glucose, 100 mg/L nitrogen (from an $NH_4Cl$ solution), and 20 mg/L phosphorus (from a $Na_3PO_4$ solution), while the other reactor was not fed. Furthermore, water losses due to evaporation were replaced daily in both reactors.

The sample from the sewage plant was analyzed for total and dissolved ATP concentration immediately prior to initiating the experiment. One week later, the contents of each reactor were also analyzed. The biomass stress index was calculated as a percentage of the total ATP for each. By reviewing the results, shown in FIG. 3, it can be seen that the biomass stress index of the sample was relatively high (greater than 30%) in the sample before it was incubated in the reactors. When the sample was incubated under starvation conditions, the biomass stress index increased to 47%. However, under favorable conditions, the biomass stress index decreased almost 10 fold to 3.9%.

Figure 3:
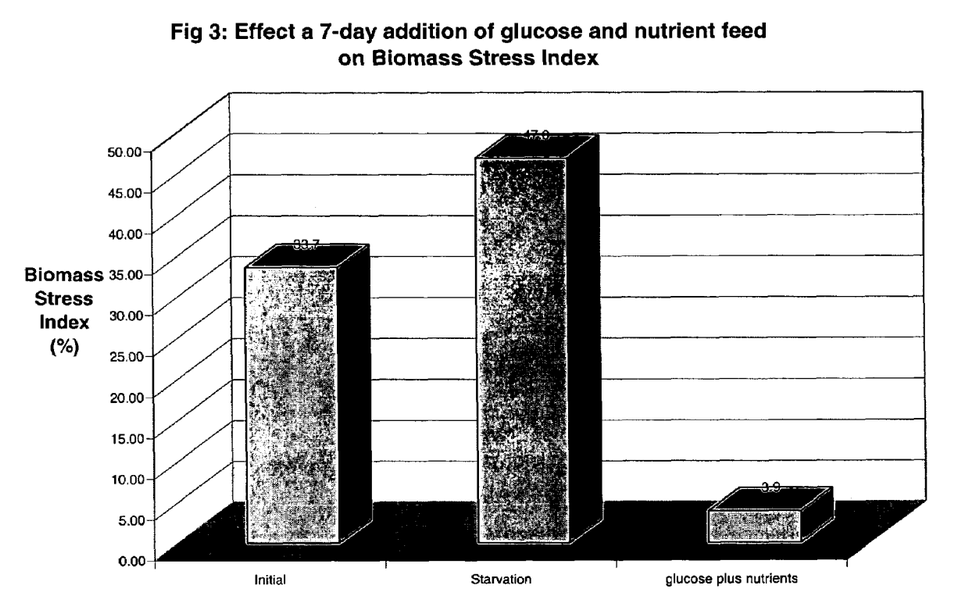
FIG. 3 illustrates the effect of a 7-day addition of glucose and nutrient feed on dissolved ATP.

During the incubation under feeding conditions, the total ATP content increased about five times. Although simply monitoring the increase of total ATP alone also demonstrates the favorable environment, determining dissolved ATP provides additional advantages. It confirms the indications of the total ATP monitoring, and it provides information on cellular health without the necessity of historical trend data.

It is thus demonstrated that the biomass stress index is useful for monitoring short-term or 'acute' stress. However, to measure chronic stresses such as nitrogen, phosphorus, and oxygen deficiency, another method that uses dissolved ATP and total ATP analyses is required.

This test is a measurement of the effect of enzymes in a sample that degrades ATP. It appears that they increase during periods of chronic stress. The method for measuring the activity of these enzymes is performed by increasing the dissolved ATP levels in the sample. This is done by adding a small quantity of a high concentration of ATP solution prepared from crystalline ATP, then measuring its removal following an incubation period after the addition. To facilitate reporting results of this test, we have named this test, dissolved ATP removal rate (DARR).

Alternatively, as discussed below, a dissolved ATP test can be performed to measure DARR.

If total ATP measurements are used, the sDARR index, which is the DARR index normalized to the amount of viable biomass in the sample, measured by determining cellular ATP, is calculated as follows:

$$sDARR_t (ng/mL/min/ng/mL) = \frac{DARR_0 - DARR_t}{t} \Big/ cATP$$

wherein, $DARR_0$ = total $ATP$ concentration in the sample after spike addition -continued = (total ATP concentration sample before spike addition +

ATP concentration added from spike);

$DARR_t$ (ng/mL)=amount of ATP remaining at time t; and cATP=cellular ATP

The same results are obtained if only dissolved ATP measurements are made for $DARR_0$ or $DARR_t$, because in the above equation, the contribution of cellular ATP is subtracted out.

An experiment showing the significance of DARR is described below as Example 3 for monitoring the stress of oxygen deficiency in an aerobic population.

EXAMPLE 3

An environment of oxygen deprivation was produced by spiking a reactor sewage plant sample with 2,000 mg/L glucose plus nitrogen and phosphate nutrients and distributing the mixture into a series of test tubes. The test tubes were capped, sealed with Parafilm™ laboratory wax, then placed horizontally in a rotary shaker to provide constant mixing at 190 rpm within the tubes. After various periods of incubation, one of the tubes was removed from the shaker and subjected to an ATP test battery consisting of total ATP, dissolved ATP, and DARR tests. The spike of ATP delivered to the subsample used for the DARR test raised the dissolved ATP concentration by 10,000 ng/mL. Ten minutes after the addition of the spike, a total ATP test was conducted on the sample.

It was assumed that as glucose was degraded by the microorganisms in the test tubes, the oxygen would be depleted. To ensure that this would occur, a dissolved oxygen uptake rate (DOUR) test was conducted prior to starting the experiment. The DOUR test showed that only 0.12 mg/L remained in the MLSS sample 20 minutes after addition of the glucose solution.

Figure 4:
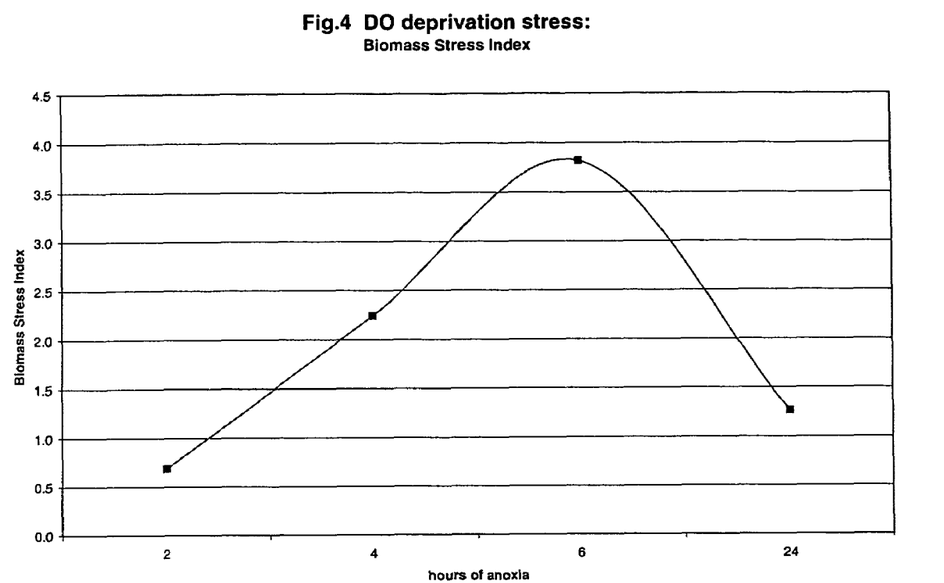
FIG. 4 illustrates the effect of stressful anoxic conditions on biomass stress index.

As shown in FIG. 4, the biomass stress index rises as anticipated on the application of stressful conditions. However, after 24 hours of continued stress, the index drops to approximately ⅓ of the peak value. Without the knowledge that the anoxic stress was still being applied and basing judgment only on the biomass stress index, one would have predicted that the environment had become less stressful.

Figure 5:
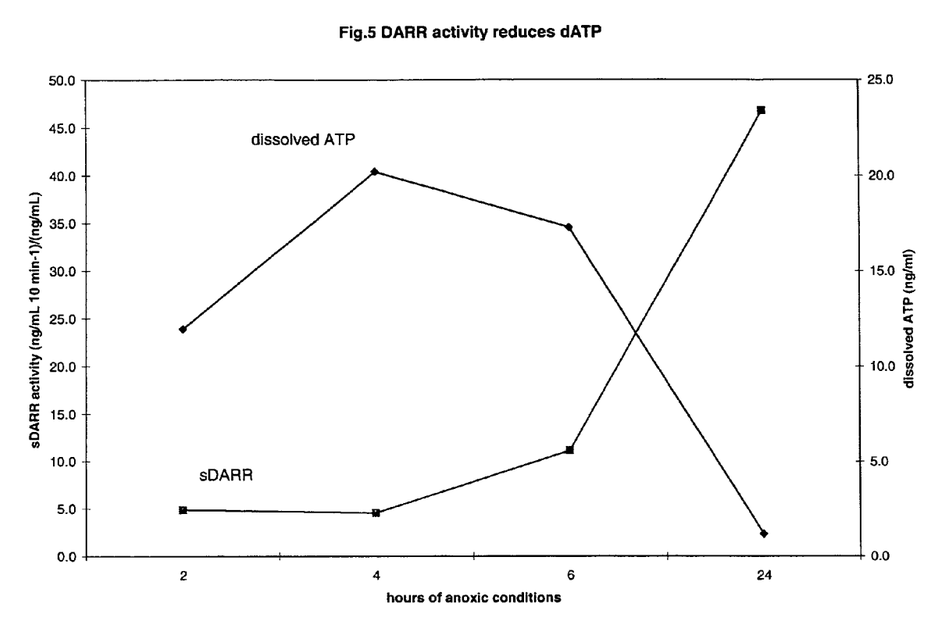
FIG. 5 illustrates the effects of stressful anoxic conditions on dissolved ATP removal rate.

However, as shown in FIG. 5, it appears that the decrease at the 24 hour incubation interval in biomass stress index was caused by an increase in DARR activity. Over the 24 hour period, DARR activity increased more than 9 times causing a corresponding 10 fold decrease in dissolved ATP.

This experiment demonstrates the importance of using a battery of ATP-based tests to accurately estimate the physiological status of the microbial population. The results also indicate that the dissolved ATP concentration of a sample at a given time represents the equilibrium value between movement of ATP from the cellular domain to the aqueous surroundings and the effect of enzymes and other sample constituents that can degrade it.

In biological processes such as activated sludge wastewater treatment, settling characteristics of the biomass are also very important. Another test was developed to monitor this aspect of the process again using dissolved and total ATP analyses.

The experiment described below as Example 4 demonstrates that monitoring settling characteristics of the biomass can reveal anoxic conditions that can lead to deterioration of settling. The experimental design was the same used for the DARR test described above. An aerated flask supplied with the same food and nutrient supplement served as a control. At various intervals over the 24 hour incubation, samples were tested for poor settling.

EXAMPLE 4

A total ATP was performed on a suspended sample. The sample was then allowed to settle. The supernatant was analyzed for dissolved ATP and an additional portion of the supernatant was analyzed for total ATP. The difference of the total ATP and dissolved ATP of the suspended sample provides the concentration of cellular ATP. The difference of the total ATP and dissolved ATP of the settled sample provides the concentration of unsettled cellular ATP. The percentage of the unsettled cellular ATP of the suspended cellular ATP is defined as planktonic ATP index.

Figure 6:
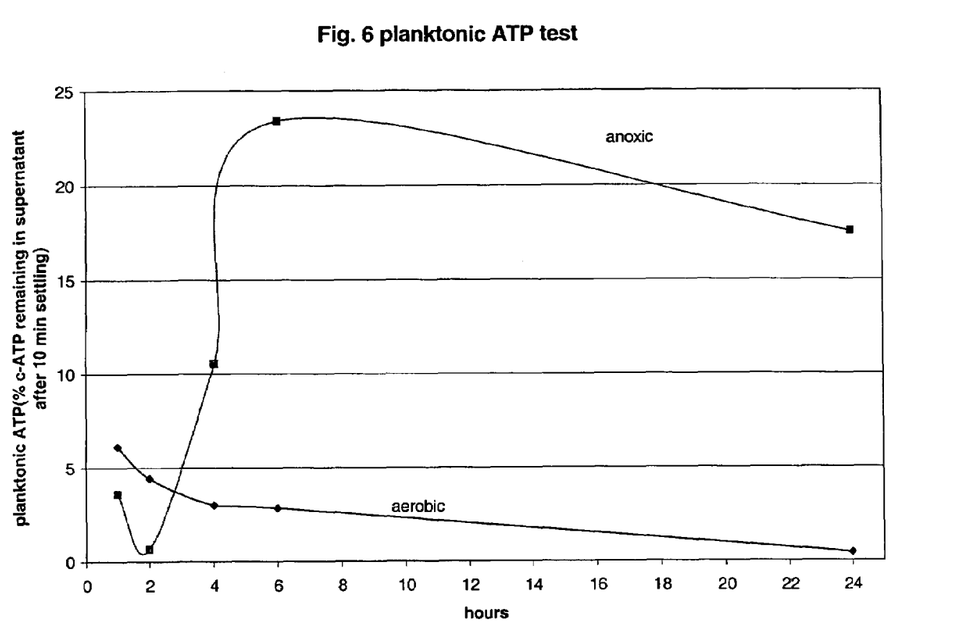
FIG. 6 illustrates the change over time of planktonic ATP.

The results of the experiment are shown in FIG. 6. It can be seen from the graph that microbial floc of the reaction began to deteriorate and release free-floating cells between 2 and 4 hours as indicated by the rise in planktonic ATP. The deterioration continued for the duration of the test. In contrast, the planktonic ATP slowly but steadily declined under the favorable aerobic conditions.

ATP analyses can also be performed on floc from a sample that has been passed through a series of sieves or other fractionating devices based on variations in size, density, and shape to gain further insights into settling properties.

Therefore by performing a battery of analyses based on both dissolved and total ATP, fundamental information about the biomass characteristics, health, and quantity can be gained. When this information is compared with operational variables together with the process outputs and statistically analyzed, plans to improve the process are likely to be more effective. These might include, but are not limited to, flow equalization, optimization of sludge return rate in activated sludge processes, nutrient optimization (which may or may not include the type of nutrients added, from nitrogen to phosphorous to micronutrients), addition of settling agents and other chemical additives, temperature, aeration and mixing optimization.

Successful and practical implementation of the above test protocols required the development of new ATP assay processes to overcome the following obstacles:

1. Unstable ATP standards
2. Unstable dissolved ATP
3. Unstable sample ATP extracts
4. Commercially available ATP releasing agents providing poor extraction efficiency
5. Wastewater being inhibitory to luciferase
6. Unstable luciferase The first 4 difficulties were overcome by developing reagents based on a high pH (pH 10-12) trisodium phosphate (TSP) buffer. The fifth difficulty was partially overcome by the TSP buffer, but also by improvements to the luciferase reagent formulation, and sample dilution. However, the high pH of the TSP buffer was incompatible with luciferase which has a pH optimum ranging between pH 7.5 to 7.75. To overcome this difficulty, a luciferase formulation was developed for measurement process that is strongly buffered in the optimum pH range, but the pH was lowered below the buffered region to pH 7.0. When combined with an ATP solution in a high pH trisodium phosphate buffer, the final pH is raised to the optimum region of the reaction.

Because ATP standard solutions are used to calibrate the luciferase reagent and luminometer, reliable standards play an essential role in ATP monitoring. This has presented an obstacle for making the ATP assay a routine laboratory test that relatively unskilled or inexperienced workers can use.

A typical approach has been to store ATP standard solutions at −20° C. or lower and thaw them on the day of use or to prepare standards fresh daily from crystalline ATP (3,4,5). A method to solve the ATP standard stability problem was described by Tobin et al. (6) who reported improved stability of ATP solutions using a high pH (pH 11.7) trisodium phosphate buffer.

However, a problem can occur if an unsuitable container is used for the ATP solution. At this pH, the walls of glass containers may start to solubilize and produce undesirable turbidity to the standard solution. Furthermore, if plastic containers are used, a problem of gas diffusion can occur. Some plastic containers readily allow diffusion of atmospheric gases into the container. High pH solutions strongly absorb carbon dioxide. As a consequence, the pH of the solution is lowered. In the case of ATP standards, lowering of the pH is unfavorable for stability due to potential for microbial growth, increase in activity of ATP-degrading enzymes, and increase of metal-catalyzed ATP hydrolysis.

Table 1 shows that stability of very dilute ATP standard solutions stored in ATP solutions in 5 mM trisodium phosphate (pH 11.6) in containers with apparently low gas permeability are stable for 20 weeks at room temperature. ATP was measured during the test period by mixing 50 microliters of a sub-sample of the ATP solution with 50 microliters of luciferase reagent. The resulting light production was measured in a Tuner Designs Model 20e luminometer.

TABLE 1

Room temperature Stability of ATP standards. Percentage of light output compared to freshly prepared standard

| ATP standard | 4 weeks | 12 weeks | 20 weeks |
| --- | --- | --- | --- |
| mL | 111.0 | 97.5 | 97.3 |
| 1,000 ng/mL | 105.4 | 97.5 | 96.0 |

It was also discovered that the trisodium phosphate buffer similar to that described by Tobin et al. (6) is useful in the measurement of dissolved ATP. The first step in the measurement of dissolved ATP is to separate the majority of the biomass from the liquid phase of the sample. This is necessary because the turbidity of a fully suspended sample quenches the light of the bioluminescent luciferase reaction. This can be accomplished by filtering the sample or simply allowing it to settle. The settling could be assisted by addition of a flocculating agent.

We also discovered that the liquor of a municipal sewage treatment reactor is inhibitory to the luciferase enzyme. Therefore, it is necessary to dilute it before mixing with luciferase for ATP measurement.

An experiment described below as Example 5 was conducted to determine the most suitable buffer for the dilution. Two buffers were compared: 5 mM trisodium phosphate buffer (pH 11.6) and N-[2-Hydroxyethyl]piperazine-N'-[2-ethanesulfonic acid] (HEPES), a buffer used in luciferase formulations adjusted to the enzyme's pH optimum (pH 7.5).

EXAMPLE 5

A sample from the reactor of a municipal sewage treatment plant was allowed to settle for 10 minutes. The supernatant was filtered in two instances then diluted in either HEPES or TSP buffer. In another instance, the supernatant was not filtered and diluted in HEPES buffer. At various time intervals, the dissolved ATP was measured by mixing 50 microliters of diluted supernatant with 50 microliters of luciferase reagent. The resulting light production was measured in a Tuner Designs Model 20e luminometer. The results shown in Table 2 below, demonstrate that without filtration, dissolved ATP decays very rapidly when HEPES is used as the diluent. The decay in HEPES is likely the effect of microbial and extracellular ATP'ases. These enzymes are inhibited in trisodium phosphate buffer. In contrast, the stability of the filtered supernatant diluted with trisodium phosphate was excellent over a 24 hour period.

TABLE 2

Stability of Dissolved ATP Diluted in HEPES and Trisodium Phosphate Buffers.

| | Time after dilution | | |
| --- | --- | --- | --- |
| | 0 hr RLU* | 1 hr RLU* | 24 hr RLU* |
| Filtered, 1/10 HEPES | 20.6 | 6.3 | 0.3 |
| Unfiltered, 1/10 HEPES | 2.0 | 0.4 | 0.7 |
| Filtered, 1/10 TSP | 23.5 | 23.3 | 22.8 |

*Relative Light Units (i.e. luminometer instrument display after ATP is assayed.)

Another experiment was conducted in a similar manner except that ATP was measured by mixing 100 microliters of diluted supernatant with 100 microliters of luciferase reagent and the resulting light production was measured in a Kikkoman LumiTester C-100.

TABLE 3

Stability of Dissolved ATP in Trisodium Phosphate Buffer.

| Minutes after dilution in TSP buffer | Filtered (RLU) | Unfiltered (RLU) |
| --- | --- | --- |
| 1 | 8515 | 8849 |
| 5 | 7940 | 9549 |
| 10 | 8269 | 9203 |
| 15 | 8269 | 9457 |
| 30 | 8390 | 8923 |

A TSP-based buffer for ATP extraction was also found very useful for extraction of ATP from microorganisms. For biological wastewater treatment process samples, significant improvements were made over the process described by Tobin et al. (6), including the elimination of using a homogenizer, increasing the TSP concentration by five fold, adding NaOH to increase the alkalinity, and substituting chloroform with the more user-friendly benzalkonium chloride.

Figure 7:
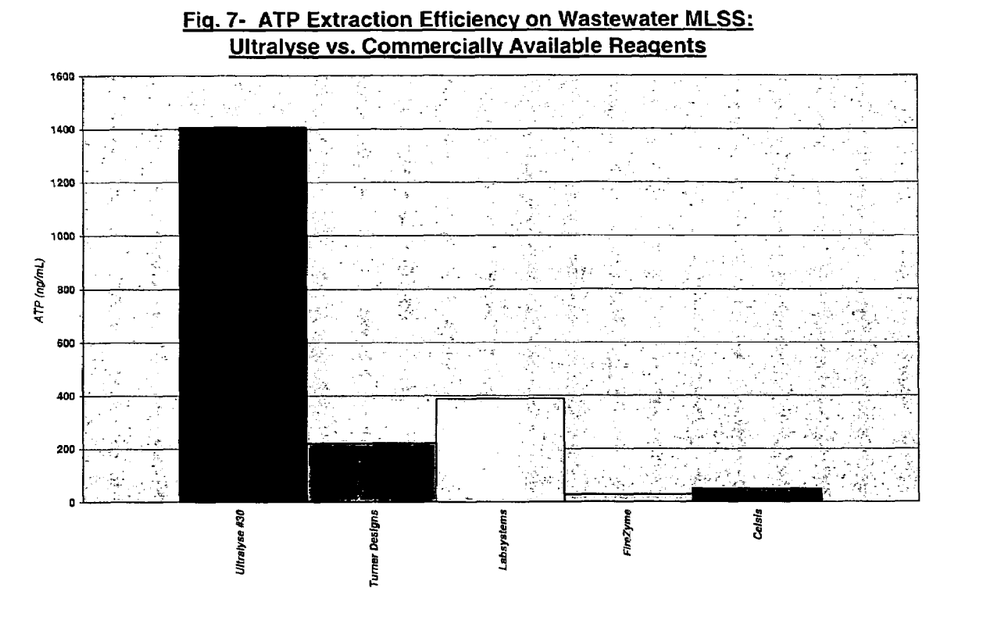
FIG. 7 illustrates a comparison of the performance of the reagent system according to the invention with several commercially available ATP releasing agents.

The benefit of these modifications compared to other commercial ATP releasing agent is shown in Example 6 described below and the results are illustrated in FIG. 7. The formulation outlined in the following Table 4 was used.

TABLE 4

Formulation Containing Trisodium Phosphate Buffer for ATP Extraction.

| Component (CAS #) | Concentration (% w/w) |
| --- | --- |
| Deionized Water | 96.08 |
| Sodium Phosphate, Tribasic Dodecahydrate | 3.66 |

TABLE 4-continued

Formulation Containing Trisodium Phosphate
Buffer for ATP Extraction.

| Component (CAS #) | Concentration (% w/w) |
|---|---|
| (10101-89-0) | |
| Benzalkonium Chloride (8001-54-5) | 0.19 |
| Sodium Hydroxide (1310-73-2) | 0.06 |

FIG. 7 shows a comparison of the performance of our formulation with several commercially available ATP releasing agents.

EXAMPLE 6

The various commercial releasing agents and our releasing agent formulation were added to a series of sub-samples taken from the reactor of a municipal sewage plant and mixed to extract the ATP from the microorganisms. In order to eliminate problems of reaction quenching, they were then diluted in deionized water and measured immediately. The final dilution of all ATP extracts was 1/306. Fifty microliters of the diluted ATP extract were mixed with 50 microliters of luciferase reagent and the resulting light was measured in a Turner Designs Model 20e luminometer. The ATP concentration in the samples was calculated from the light measurement of both the sample and a similar measurement of an ATP standard solution of known concentration.

The results demonstrate the superior efficiency of our TSP-based releasing agent, UltraLyse™ 30 compared to other commercial reagents. An efficient extraction reagent is not only important with respect to total ATP measurement. Incomplete extraction will also interfere with the accuracy of the biomass stress index and cellular ATP measurements because total ATP is a component of these parameters.

In addition to providing superior extraction efficiency, the use of the TSP-based releasing agent produces extracts that are relatively stable. This permits the analyst to delay measurement of the extract until it is most convenient. It also could facilitate automated or mechanized analytical processes.

TABLE 5

Stability of ATP extracts in the Trisodium
Phosphate Buffer Formulation.

| Days of refrigerated storage In UtlraLyse 30 | ATP recovery (% of initial) |
|---|---|
| 1 | 98 |
| 3 | 96 |
| 7 | 91 |

Despite the many advantages provided by the high pH TSP buffer, it has one problem. The pH of the buffer is much higher than the optimum for the activity of luciferase which is approximately pH 7.4 to 7.8.

We discovered that this problem can be overcome by using a luciferase buffer that has a pK near the optimum of the luciferase enzyme and then lowering the pH to approximately pH 7.0. Thus, when a solution of ATP in high pH TSP buffer is added to the luciferase reagent the pH is raised to the optimum region. Using a pH of 7.0 for the luciferase preparation has a second benefit. Luciferase is more stable at pH levels lower than its optimum for activity (8).

The stability of the luciferase can be further improved by the addition of other stabilizing agents such as a chelating agent like ethylenediamine tetra acetic acid (EDTA), protein-based stabilizers such as bovine serum albumin (BSA), a reducing agent to protect sulfhydryl groups such as dithiothreitol and a hydrogen bond stabilizer such as trehalose (8-10).

Foote and Grant (11) also teach the stabilization of luciferase in the presence of a polyol such as trehalose and glycerol when adjusted to a pH lower than the optimum for activity. However, the formulations described by Foote and Grant use weak buffers, with a pK at the storage pH. Mixing such formulation with ATP in a high pH TSP buffer would be problematic because there would be a tendency for the reaction pH to fall outside the optimum range for activity.

In addition to contributing to the stabilization of luciferase, EDTA provides protection of the enzyme from inhibition of heavy metals that are frequently encountered in wastewater samples. Therefore, it is advantageous to maximize the EDTA concentration in the luciferase reagent.

Table 6 shows the results of an experiment described below as Example 7 used to determine the maximum EDTA concentration that can be used in a luciferase formulation without inhibiting luciferase activity. The magnesium salt of EDTA was used to ensure that magnesium would be available as a cofactor for the luciferase. The test was conducted by spiking aliquots of luciferase with a concentrated solution of Mg/EDTA and testing luciferase activity by adding ATP standard (1,000 ng/mL). Fifty microliters of ATP standard were mixed with 50 microliters of luciferase reagent and the resulting light was measured in a Turner Designs Model 20e luminometer.

TABLE 6

Effect of Increasing the Magnesium-EDTA
Concentration on Luciferase Activity.

| Final Mg/EDTA in Luciferase Reagent (g/L) | Instrument Display After Mixing Luciferase with ATP |
|---|---|
| 1.7 | 292 |
| 3.4 | 280 |
| 5.1 | 206 |
| 6.8 | 169 |
| 8.4 | 119 |
| 10.1 | 115 |
| 11.8 | 75 |
| 13.5 | 88 |
| 15.2 | 70 |
| 16.9 | 58 |

The results indicate that 3.4 g/L of the chelating agent can be added without serious loss of enzyme activity.

EXAMPLE 7

Two formulations having the composition outlined below in Table 6 were tested for their stability at room temperature and under refrigerated conditions. One formulation was prepared using a luciferase from Kikkoman (LUC-T) that had been purified from cultures of E. coli into which the genes of the firefly luciferase had been inserted and altered to produce a more heat-stable enzyme, while the other formulation contained luciferase from Sigma-Aldrich that had been purified directly from fireflies. At various time intervals 50 microliter sub-samples of each formulation were removed, mixed with 50 microliters of a 1 ng/mL ATP standard and the resulting light was measured in a Turner Designs Model 20e luminometer. The results were expressed as a percentage of the reading obtained at the beginning of the experiment.

Both formulations in the experiment contained 40 micrograms luciferase per mL and 100 micrograms luciferin per mL and were adjusted to pH 7.0. The formulations consisted of the components outlined below in Table 7.

TABLE 7

Example of Luciferase Formulation

| Component | | Quantity |
|---|---|---|
| Deionized water | mL | 100 |
| HEPES disodium | g | 0.6508 |
| Mg/EDTA | g | 0.346 |
| Trehalose | g | 10 |
| Dithiothreitol | g | 0.0133 |
| Bovine serum albumin | g | 0.1 |
| Magnesium sulphate•7H$_2$O | g | 0.949 |
| D-luciferin | μg | 100 |
| Luciferase | μg | 40 |

Figure 8:
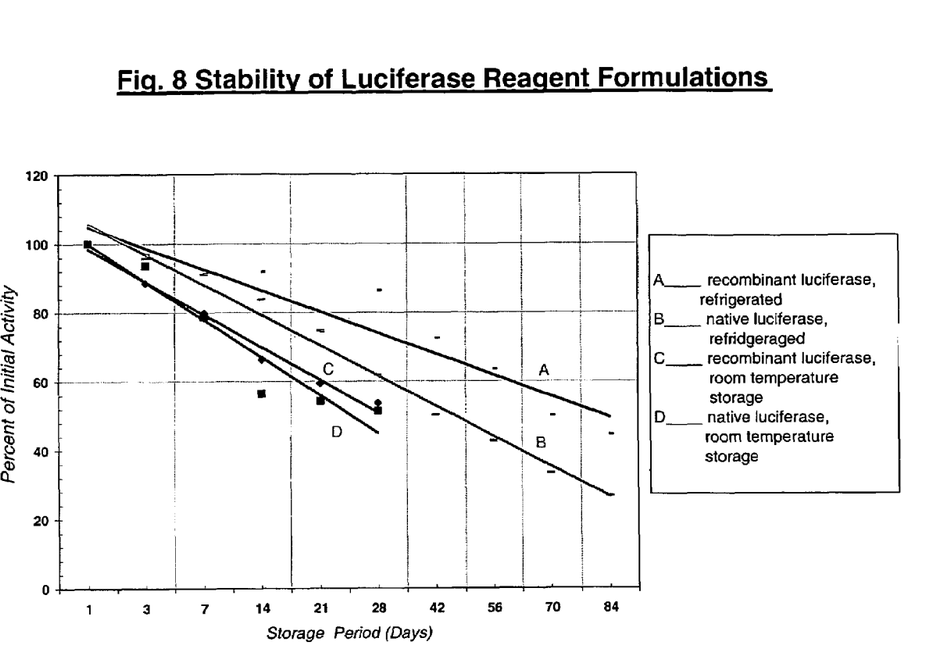
FIG. 8 illustrates the stability of luciferase reagent formulations according to the invention.

FIG. 8 shows that the activity of both formulations are similar at room temperature, illustrating an excellent stability over a three week period at which time approximately 50% of the enzyme activity still remains. By comparison, Sigma-Aldrich has their own luciferin/luciferase ATP assay formulation that they claim is stable for 2 weeks when rehydrated and stored under refrigerated conditions, and do not suggest to leave the enzyme reagent at room temperature.

The use of refrigerated storage conditions appears to be advantageous for the recombinant luciferase. FIG. 8 shows that the half-life of the activity is almost doubled.

Accordingly, the invention provides a method for optimizing biological processes performed by correlating operational variables of a process together with the process outputs and a battery of analyses based on the measurement of dissolved or extracellular ATP in conjunction with the measurement of total ATP (dissolved plus cellular ATP). The operational variables may include but are not limited to food (biological oxygen demand (BOD), biodegradable substrate analytical profiles), pH, acidity, alkalinity, temperature, conductivity, nutrients, other chemical addition, dissolved oxygen, pressure, and toxic substance concentration. The process outputs may include but are not limited to BOD removal, nutrient consumption, heat, concentration and production rate of carbon dioxide, methane, hydrogen, hydrogen sulfide, volatile fatty acids and other organic acids, alcohols, suspended solids, and volatile suspended solids.

The invention also provides for a method in which total ATP in a sample from a biological process may be measured by adding an ATP releasing agent to a completely mixed sub-sample, then assaying for ATP. Preferably, the resulting mixture can be diluted prior to assaying for ATP.

The dissolved ATP in a sample from a biological process may be measured by separating the biological solids from the sampe, taking a sub-sample of the liquor, and assaying for ATP. The sub-sample can be diluted prior to assaying for ATP.

The cellular ATP in a sample from a biological process may be determined by measuring total and dissolved ATP and subtracting the dissolved ATP value from the total ATP value.

The biomass stress index of microorganisms in a sample from a biological process may be determined by measuring total ATP and dissolved ATP and calculating the ratio of the dissolved ATP to the total ATP. The biomass stress index of microorganisms in a sample from a biological process also may be determined by measuring and calculating the dissolved ATP and the cellular ATP and calculating the ratio of the dissolved ATP to the cellular ATP.

The dissolved ATP removal rate in a sample from a biological process may be determined by measuring the disappearance of a dissolved ATP spike added to the biomass suspension. The dissolved ATP spike can be about 1 to 100 times higher than the total ATP of the sample. The preferred dissolved ATP spike can be about 10 times higher than the total ATP of the sample. DARR may be normalized to the total ATP or cellular ATP content of the sample prior to the addition of the ATP spike.

The quantity of free-floating or planktonic biomass may be estimated by measuring the cellular ATP in a sample from a biological process that has been allowed to settle. The planktonic index may be determined by measuring the total and/or cellular ATP in a sample from a biological process that has been allowed to settle and calculating the fraction that this ATP represents of the total and/or cellular ATP of the completely mixed sample.

The biomass floc dispersion index may be determined by measuring the total and/or cellular ATP contained in pin-sized floc and free-floating or planktonic cells by using a sieve to separate them from the other microorganisms in the sample and then measuring the total and/or cellular ATP.

The bulking floc may be measured by sieving or treating a sample to separate floc containing excessive quantities of bulking filamentous bacteria and assaying the total and/or cellular ATP of this component of the sample.

The biomass growth index may be determined by adding nutrients and adding biomass from a biological process to the process influent or effluent water of the biological process and measuring the growth rate of the microorganisms by measuring total and/or cellular ATP.

The toxicity index may be determined by adding nutrients and adding biomass from a biological process to the process influent or effluent water of the biological process and measuring total and/or cellular ATP to determine the growth rate or decrease in total and/or cellular ATP or increase in biomass stress index of the microorganisms.

The activity of the grazing population of a floc may be measured by adding a suspension of planktonic or free-floating their bacteria to the sample and measuring the rate of their disappearance by periodically measuring the planktonic ATP over timed intervals.

The biomass may be separated from the sample by allowing the sample to settle by gravity or centrifuging, flocculating, or filtering it.

In the method according to the invention, ATP may be measured in a luminometer by a bioluminescent reaction produced by mixing an ATP solution containing a high pH (about pH 10-12) phosphate buffer with a reagent containing luciferin, luciferase, and magnesium cofactor dissolved in a buffer with a pK of about 7.5 to 8.5 but adjusted to about pH 6-7.2. The ATP solution used may be an ATP standard solution stored in a container with low gas permeability. The preferred phosphate can be trisodium phosphate at a concentration of about 5 mM.

The luciferase may be immobilized on a support substrate and may be re-used for more than one analysis. The luciferase may be a recombinant luciferase. The luciferase reagent may contain at least one of the following components: an enzyme hydrogen-bond stabilizer such as trehalose, glycerol, or glycol; a chelating agent such as EDTA, a protein-based enzyme stabilizer e.g. BSA, casein; and a reducing agent to maintain luciferase sulfhydryl groups in a reduced form, e.g. dithiothreitol, mercaptoethanol. EDTA may be present in an amount of between about 0.03% to 1.3% by weight of the luciferase reagent.

The source of the ATP solution may be the extracellular ATP in a suspension containing microorganisms. The sample may be centrifuged or allowed to settle with or without the assistance of a flocculating agent and the supernatant may be mixed with a high pH phosphate buffer. The preferred phosphate can be trisodium phosphate at a concentration of about 5 mM. The sample may be filtered and the filtrate can be mixed with a high pH phosphate buffer. The preferred phosphate can be trisodium phosphate at a concentration of 5 mM.

The source of the ATP solution may be a sample containing microorganisms that have been treated with an ATP releasing agent containing a high pH phosphate buffer. The releasing agent may be composed of phosphate buffer and a cationic or non-ionic surfactant. The pH of the releasing agent can be greater than about pH 9.9 and preferably about pH 11.1 to 11.7. The preferred phosphate can be trisodium phosphate at a concentration of between about 0.5 mM and 500 mM. Preferably for biological wastewater treatment applications, the concentration can be between about 5-100 mM. The concentration of the surfactant can be about 100 to 10,000 mg/L. In the case where benzalkonium chloride is the cationic surfactant and the application is a biological wastewater treatment plant, the preferred concentration can be about 1,000-4,000 mg/L.

The releasing agent may also be composed of trisodium phosphate, a cationic or non-ionic surfactant, and sodium hydroxide. The pH of releasing agent can be greater than about pH 9.9 and preferably about pH 11.1 to 11.7. The preferred phosphate can be trisodium phosphate at a concentration of between about 0.5 mM and 500 mM. Preferably for biological wastewater treatment applications, the concentration can be between about 5-100 mM. The concentration of the surfactant may be about 100 to 10,000 mg/L. In the case where benzalkonium chloride is the cationic surfactant and the application is a biological wastewater treatment plant, the preferred concentration can be about 1,000-4,000 mg/L. The concentration of sodium hydroxide may range from about 100 to 10,000 mg/L, but the preferred concentration for samples from biological wastewater treatment applications can be about 600 mg/L.

The sample may be filtered and the filter can be treated with a releasing agent containing a high pH phosphate buffer. The preferred phosphate buffer can be trisodium phosphate at a concentration between about 0.5 mM and 500 mM. Preferably for biological wastewater treatment applications, the concentration can be between about 5-100 mM.

The sample may also be filtered, and the filtrate may be treated with organic solvent, then treated with high pH phosphate buffer or a releasing agent containing a high pH phosphate buffer. The preferred phosphate buffer can be trisodium phosphate at a concentration of between about 0.5 mM and 500 mM. The dissolved ATP from microorganisms may be enzymatically or chemically removed prior to addition of the releasing agent.

According to the invention, the reagents for the process may be used in test kits.

Data from the luminometer may be statistically analyzed using a computer program and the analysis may be used to automatically adjust the process operations.

Process operations may include but are not limited to flow equalization, aeration, pH adjustment, mixing, sludge return rate, effluent return rate, nutrient and other chemical addition.

Preferred buffers for the luciferase reagent may be N-[2-Hydroxyethyl]piperazine-N'-[2-ethanesulfonic acid] (HEPES); N-[tris(hydroxymethy)methyl]glycine; and N-[2-hydroxy-1,1-bis(hydroxymethyl)ethyl]glycine (TRICINE). The preferred concentration may be about 0.025 to 0.075 M and the preferred pH can be about pH 6.5 to 7.0.

While the foregoing description has described the best mode currently contemplated for practicing the invention, the scope of the invention is not intended to be limited by this description. Various alternative combinations of the reagent system are contemplated as being included within the scope of the following claims particularly pointing out and distinctly claiming the present invention.

REFERENCES

1. Patterson, J. W., Brezonik, P. L., and Putnam, H. D. (1970) Measurement and significance of adenosine triphosphate in activated sludge. Environ. Sci. Technol. 4(7) 569-575.
2. Roe, P. C. Jr. and Bhagat, S. K. (1982) Adenosine triphosphate as a control parameter for activated sludge processes. J. Wat. Pollut. Cont. Fed. 54, 244-254.
3. Archibald, F., Méthot, M, Young, F., and Paice, M. G. (2001) A Simple System To Rapidly Monitor Activated Sludge Health And Performance. Wat. Res. 35 (10) 2543-2553.
4. Annual Book of ASTM Standards (1989). Standard Method for Adenosine Triphosphate (ATP) Content of Microorganism in Water. Volume 11.02 Water (II) 455-458.
5. Sigma Chemicals (1988). Adenosine 5'-Triphosphate (ATP) Bioluminescent Assay Kit. Technical Bulletin # BAAB-1.
6. Promega Corporation (2001). rLuciferase/Luciferin Reagent Bioluminescence Detection Reagent for ATP Measurement. Technical Bulletin #268.
7. Tobin R. S., Ryan J. F. and Afghan B. K. (1978) An improved method for the determination of adenosine triphosphate in environmental samples. Water Res. 12, 783-792.
8. Deluca, M. (1975) ATP Methodology Seminar, SAI Technology Co., San Diego.
9. Lundin, A. (1993) Optimised Assay of Firefly Luciferase with Stable Light Emission in Bioluminescence and Chemiluminescence Status Report. A. A. Szaly, L. J. Kricka, and P. Stanley ed., Wiley, pp. 291-295.
10. Wang, C. Y. and Andrale, J. D. (1993) Interfacial Behavior of Firefly Luciferase in Bioluminescence and Chemiluminescence Status Report. A. A. Szaly, L. J. Kricka, and P. Stanley ed., Wiley, pp. 99-103.
11. Foote, N. P. M. and Leonard, G. P. (1994) Bioluminescence Reagent Formulation. Published international patent application number WO9411528.

We claim as my/our invention:

1. A method of estimating cellular adenosine triphosphate (ATP) based on the actual measurement of both extracellular ATP and total ATP in a sample, which comprises the step of applying a reagent system to the sample, the reagent system comprising:
   a first reagent which includes a high pH having a range of about pH 9.9 to 12 phosphate buffer; and
   a second reagent which includes luciferase, luciferin, a magnesium salt and an enzyme stabilizer, said second reagent having a low pH range of about 6 to 8.5 and a buffer with a pK which is near the optimum pH for activity of luciferase;
   wherein the application of said first and second reagents to said sample is operable for measuring extracellular ATP in said sample, and wherein the application to said sample of said first reagent together with a cationic surfactant and said second reagent is operable for measuring total ATP in said sample.

2. The method of claim 1, wherein said high pH phosphate buffer comprises trisodium phosphate.

3. The method of claim 1, wherein said first reagent further comprises a cationic surfactant.

4. The method of claim 1 or 3, wherein said first reagent further comprises a base.

5. The method of claim 1, wherein said cationic surfactant is a quaternary ammonium salt.

6. The method of claim 5, wherein said quaternary ammonium salt is benzalkonium chloride.

7. The method of claim 4, wherein said base is sodium hydroxide.

8. The method of claim 1, wherein said first reagent has a pH which is greater than about 9.9.

9. The method of claim 1, wherein said first reagent has a pH of about 11.1 to 11.7.

10. The method of claim 1, wherein the second reagent further comprises a chelating agent.

11. The method of claim 1, wherein said stabilizer is selected from a combination of an enzyme hydrogen-bond stabilizer, a protein enzyme stabilizer, and a reducing agent.

12. The method of claim 11, wherein the combination comprises trehalose, bovine serum albumin and dithiolthreitol.

13. The method of claim 10, wherein said chelating agent is ethylenediamine tetra acetic acid (EDTA).

14. The method of claim 1, wherein the pH of the second reagent is adjusted to pH 6 to 8.5.

15. The method of claim 1, wherein the pK of the second reagent is about 7.5 to 8.5.

16. The method of claim 13, wherein the pK of the second reagent is about 7.5 to 7.75.

17. The method of claim 1, wherein the pH of the second reagent is adjusted to about pH 7.0.

18. The method of claim 1, wherein luciferase is selected from native luciferase and recombinant luciferase.

19. The method of claim 18, wherein said native luciferase is obtained directly from fireflies.

20. The method of claim 1, wherein luciferase is immobilized on a support substrate.

21. The method of claim 20, wherein said support substrate is a transparent material or a translucent material selected from the group consisting of glass and silica.

22. The method of claim 20, wherein luciferase is reusable.

23. The method of claim 1, wherein said buffer of the second reagent is selected from the group consisting of N-[2-hydroxyethyl]piperazine-N'-[2-ethanesulfonic acid] (HEPES), N-[tris(hydroxymethyl)methyl]glycine (TRICINE), N-[2-hydroxy-1,1-bis(hydroxymethyl)ethyl] glycine and combinations thereof.

24. The method of claim 1, wherein the second reagent is reconstituted from a freeze-dried formulation.

25. The method of claim 2, wherein the trisodium phosphate is at a concentration of about 0.5 to 500 mM.

26. The method of claim 2, wherein the trisodium phosphate is at a concentration of about 5 mM.

27. The method of claim 10, wherein said chelating agent is in an amount of about 0.03 to 1.3% by weight of the second reagent.

28. The method of claim 3, wherein said cationic surfactant is at a concentration of about 100 to 10,000 mg/L.

29. The method of claim 3, wherein said cationic surfactant is at a concentration of about 1000 to 4000 mg/L.

30. The method of claim 4, wherein said base is at a concentration of about 100 to 10,000 mg/L.

31. The method of claim 4, wherein said base is at a concentration of about 600 mg/L.

* * * * *